(12) United States Patent
Heist et al.

(10) Patent No.: US 7,395,120 B2
(45) Date of Patent: Jul. 1, 2008

(54) TELESCOPING, DUAL-SITE PACING LEAD

(75) Inventors: E. Kevin Heist, Brookline, MA (US); Jagmeet P. Singh, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 178 days.

(21) Appl. No.: 11/145,077

(22) Filed: Jun. 3, 2005

(65) Prior Publication Data

US 2006/0064150 A1 Mar. 23, 2006

Related U.S. Application Data

(63) Continuation-in-part of application No. 10/918,787, filed on Aug. 13, 2004, now abandoned.

(51) Int. Cl.
*A61N 1/00* (2006.01)

(52) U.S. Cl. .................................................. 607/123

(58) Field of Classification Search .................. 607/123
See application file for complete search history.

(56) References Cited

U.S. PATENT DOCUMENTS

| | | | |
|---|---|---|---|
| 5,172,694 A | 12/1992 | Flamming et al. | |
| 5,755,766 A | 5/1998 | Chastain et al. | |
| 5,782,898 A | 7/1998 | Dahl et al. | |
| 5,925,073 A | 7/1999 | Chastain et al. | |
| 6,064,902 A | 5/2000 | Haissaguerre et al. | |
| 6,136,021 A | 10/2000 | Tockman et al. | |
| 6,584,362 B1 | 6/2003 | Scheiner et al. | |
| 6,988,007 B1 | 1/2006 | Morgan et al. | |
| 2002/0077685 A1* | 6/2002 | Sundquist et al. | 607/116 |
| 2002/0116043 A1 | 8/2002 | Garibaldi et al. | |
| 2003/0023295 A1* | 1/2003 | Osypka | 607/122 |
| 2003/0055476 A1* | 3/2003 | Vinup et al. | 607/117 |
| 2004/0064176 A1 | 4/2004 | Min et al. | |
| 2004/0082986 A1 | 4/2004 | Westlund et al. | |
| 2006/0064150 A1 | 3/2006 | Heist et al. | |

OTHER PUBLICATIONS

Fei et al., "Effects of Multisite Ventricular Pacing on Cardiac Function in Normal Dogs and Dogs with Heart Failure", Journal of Cardiovascular Electrophysiology, vol. 10, No. 7, Jul. 1999, pp. 935-946.
Pappone et al., "Cardiac pacing in heart attach patients with left bundle branch block: impact of pacing site for optimizing left ventricular resynchronization", Italian Heart Journal, Offical Journal of the Italian Federation of Cardiology, vol. 1, No. 7, Jul. 2000, pp. 464-469.

* cited by examiner

*Primary Examiner*—Carl H. Layno
*Assistant Examiner*—Jon-Eric Moraes
(74) *Attorney, Agent, or Firm*—Fish & Richardson P.C.

(57) ABSTRACT

A lead with a proximal electrode and a telescoping distal electrode enables dual-site electrical pacing or stimulation of a heart or another organ. The lead includes an outer tube with a proximal electrode and an inner tube connected to a distal electrode. The inner tube is concentric and slides inside the outer tube. This design enables the proximal electrode to be placed at a desired location by threading the lead along a guide wire, and then extending the distal electrode a variable distance beyond the proximal electrode.

20 Claims, 6 Drawing Sheets

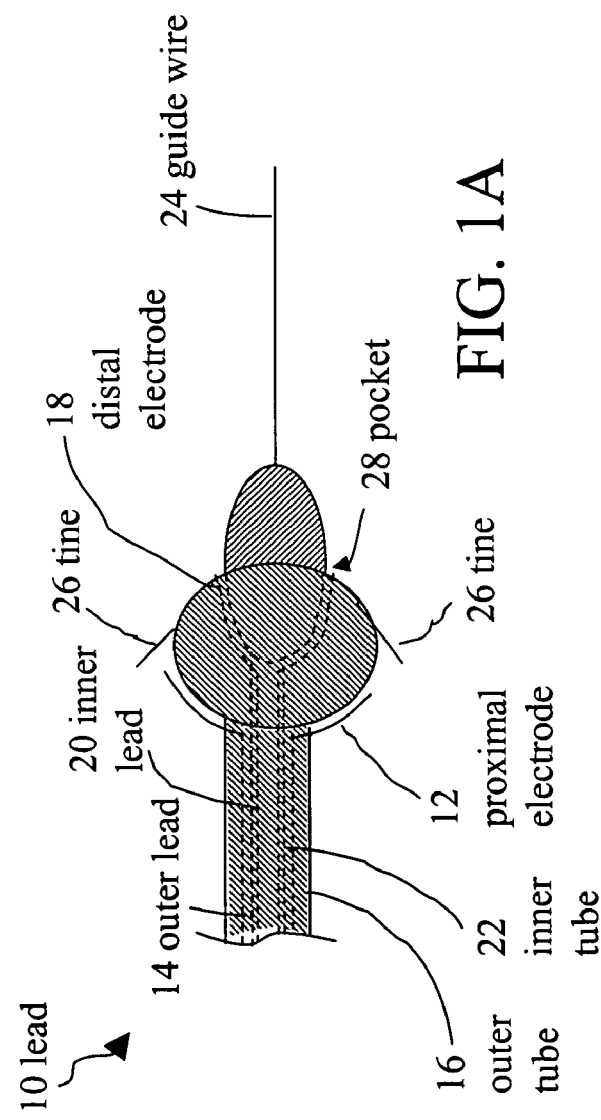
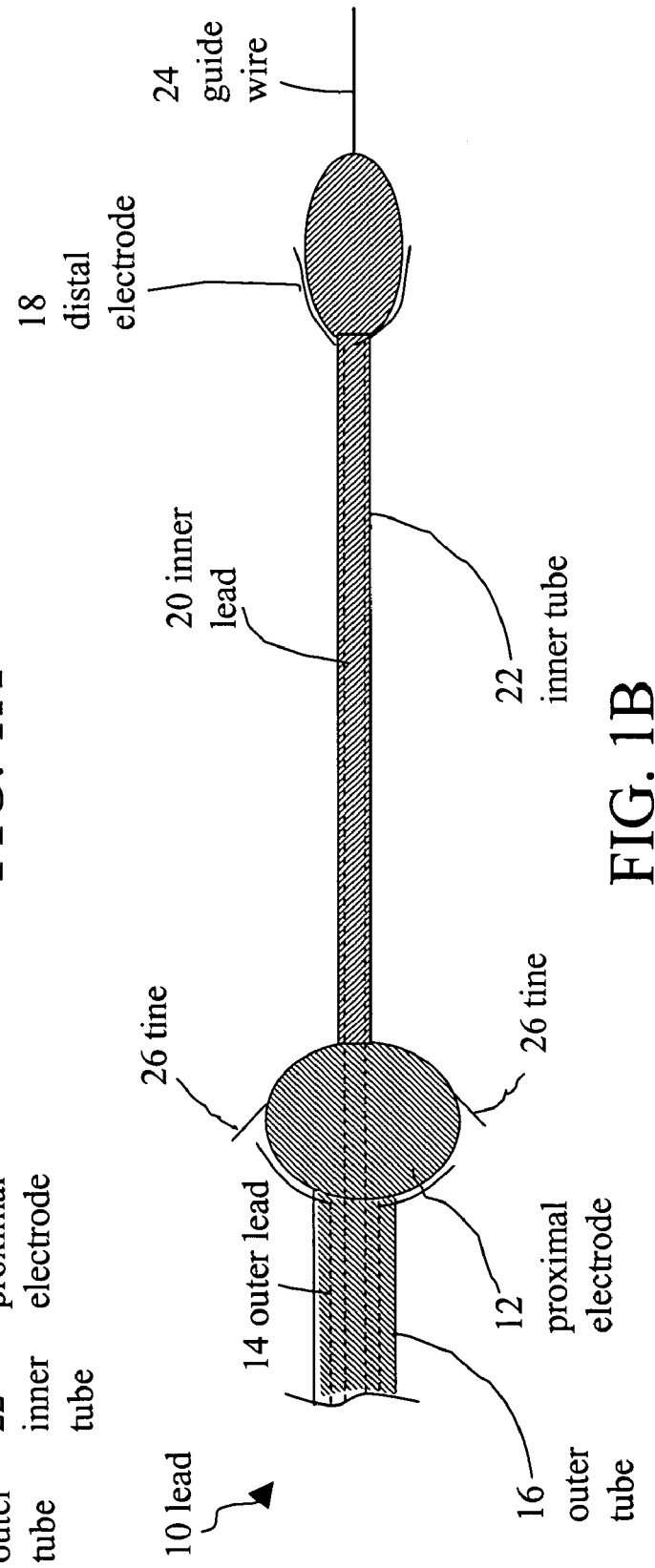

TELESCOPING, DUAL-SITE PACING LEAD

RELATED APPLICATION

Under 35 U.S.C. 120, this application is a continuation-in-part application and claims the benefit of non-provisional application Ser. No. 10/918,787, filed Aug. 13, 2004, now abandoned.

TECHNICAL FIELD

This invention relates to telescoping, dual-site pacing leads for heart pacing and other applications.

BACKGROUND

Biventricular pacemakers pace stimulate the left and right ventricles simultaneously. This enables the left ventricle (LV) to pump blood more efficiently.

The coronary sinus is a vein that flows from tributary branches, such as the lateral venous branch and the middle cardiac vein, to the right atrium of the heart. A lead from a biventricular pacemaker lead is often inserted in one of these tributary branches. Such leads are typically inserted into the coronary sinus through the subclavian vein and/or cephalic vein, both of which are easily accessed through a chest wall of a patient. The leads pass through the right atrium and into the coronary sinus.

Currently, biventricular pacing systems use single site pacing of the left ventricle ("LV") to facilitate cardiac resynchronization therapy. There is data to suggest that dual site LV pacing can benefit patients with poor heart function. This dual site pacing provides simultaneous or sequential stimulation of two LV sites, thereby recruiting more myocardium, reducing myocardial dyssynchrony and enhancing cardiac contractility.

There is also data to suggest that dual site electrical tissue stimulation can be useful for treatment of neurologic disorders such as Parkinson's disease and paralysis, neuromuscular disorders such as multiple sclerosis and amyotrophic lateral sclerosis, and gastrointestinal disorders such as amotility.

SUMMARY

The invention is based, in part, on the discovery that a lead with a proximal electrode and a telescoping distal electrode enables better electrical pacing or stimulation of a heart or another organ. The lead includes an outer tube with an outer lead connected to the proximal electrode. An inner tube with an inner lead is connected to the distal electrode. The inner tube is concentric and slides inside the outer tube. This design enables the proximal electrode to be placed at a desired location by threading the lead along a guide wire. Next, the distal electrode can be extended a variable distance beyond the proximal electrode by threading along an additional length of the same guide wire. This lead can be used to provide simultaneous or sequential pacing at left ventricular sites in a patient's heart.

In general, the invention features leads including a first tube; a first lead conductor having a portion extending through the first tube; a proximal electrode disposed at a distal end of the first tube, the proximal electrode being in electrical communication with the first lead conductor; a second tube arranged slideably within the first tube, the second tube forming a central lumen sized to accommodate a guide wire; a second lead conductor extending through the second tube; a distal electrode disposed at a distal end of the second tube, the distal electrode being in electrical communication with the second lead conductor; and a bipolar connector attached to the first and second lead conductors and configured to be removably attached to a pacing control system.

In certain embodiments, the bipolar connector is configured to transmit first and second signals from the pacing control system to the first and second lead conductors, respectively. In other embodiments, the connector includes first and second connecting conductors that are attached to the first and second lead conductors and configured to be received by a port in the pacing control system; and a housing that at least partially encloses the first and second connecting conductors. In some embodiments, the first and second connecting conductors are arranged coaxially or twinaxially. In certain embodiments, the bipolar connector complies with at least one of: an IS-1 international pace maker standard, a VS-1 standard, a VS-1A standard, and a VS-1B standard.

In certain embodiments, the second tube can be longer than the first tube, the first tube can have a first appendage, and the proximal electrode can be attached to an outer surface of the first appendage. In other embodiments, the distal end of the second tube can have a second appendage, and the distal electrode can be attached to an outer surface of the second appendage. The first and second appendages can each include a radio-opaque marker, and one or both of the proximal and the distal appendages can each further include one or more tines. In certain embodiments, the first and/or second conductors are in the shape of a coil, and the lead can further include a fixation device to prevent motion of the second tube relative to the first tube.

In some examples, the first and second conductors can be bipolar, and the distal electrode can be extended approximately at least five centimeters beyond the proximal electrode. In certain embodiments, the first and second tubes are electrically insulating.

In other embodiments the lead includes a third tube having a distal end attached to the first tube and a proximal end attached to the second tube such that the first lead conductor extends through portions of the first, second, and third tubes, and passes through the openings in the first and second tubes.

In another aspect, the invention also includes an implantable biventricular pacemaker that includes the lead.

The invention also features methods for positioning the leads in the heart, by moving a guide wire through a blood vessel against normal flow of blood to a desired section of the blood vessel; threading the lead onto the guide wire through the blood vessel to the desired section of the blood vessel in the heart; sliding the second conductor in a distal direction such that the distal electrode moves distally away from the proximal electrode; moving the distal electrode to a tributary branch of the blood vessel; securing the fixation device; and removing the guide wire.

In these methods, sliding the second lead in a distal direction can include sliding the distal electrode up to approximately five centimeters away from the proximal electrode. The methods can also include the use of a detector, such as an x-ray detector, to monitor the position of radio-opaque markers on the guide wire and proximal and distal electrodes of the lead. In certain embodiments, the blood vessel in which the lead is positioned is a set of arterial or venous tree branches such as a coronary sinus or an intra-cerebral vein, and the methods can include pacing the heart by applying an electric charge to the first and second conductors.

These and other embodiments may have one or more of the following advantages that enhance the ability of currently available pacing techniques to optimize cardiac function. These advantages include the ability to perform dual site pacing with a single transvenous lead design. This single lead design allows two pacing leads to be inserted in one operation. The two pacing leads are concentric, which reduces inherent, internal twisting of the lead and makes the surgical insertion easier. The two electrodes on the leads are located on oval-shaped appendages that can be positioned to stay in place for a long period of time in a vein such as an LV tributary branch. The ability to provide simultaneous or sequential pacing at two sites allows for optimization of LV apical and basal delay. There is an adjustable distance between the two pacing sites. The design also allows pacing to be maintained in case of micro-dislodgement of one electrode lead, due to the availability of the two pacing sites. The connector design allows a single bipolar connector to be used for connecting the proximal and distal electrodes to a pacing control system (e.g., an implantable biventricular pacemaker). These embodiments are also compatible with existing lead implant equipment and techniques. For example, in certain embodiments, the bipolar connector complies with an IS-1 international pace maker standard.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG 1A is a cross-sectional view of a lead with a proximal electrode and a distal electrode, the distal electrode in a retracted position next to the proximal electrode.

FIG. 1B is a cross-sectional view of the lead of FIG. 1A, with the distal electrode extended away from the proximal electrode.

DETAILED DESCRIPTION

Lead Design

Figure 2:
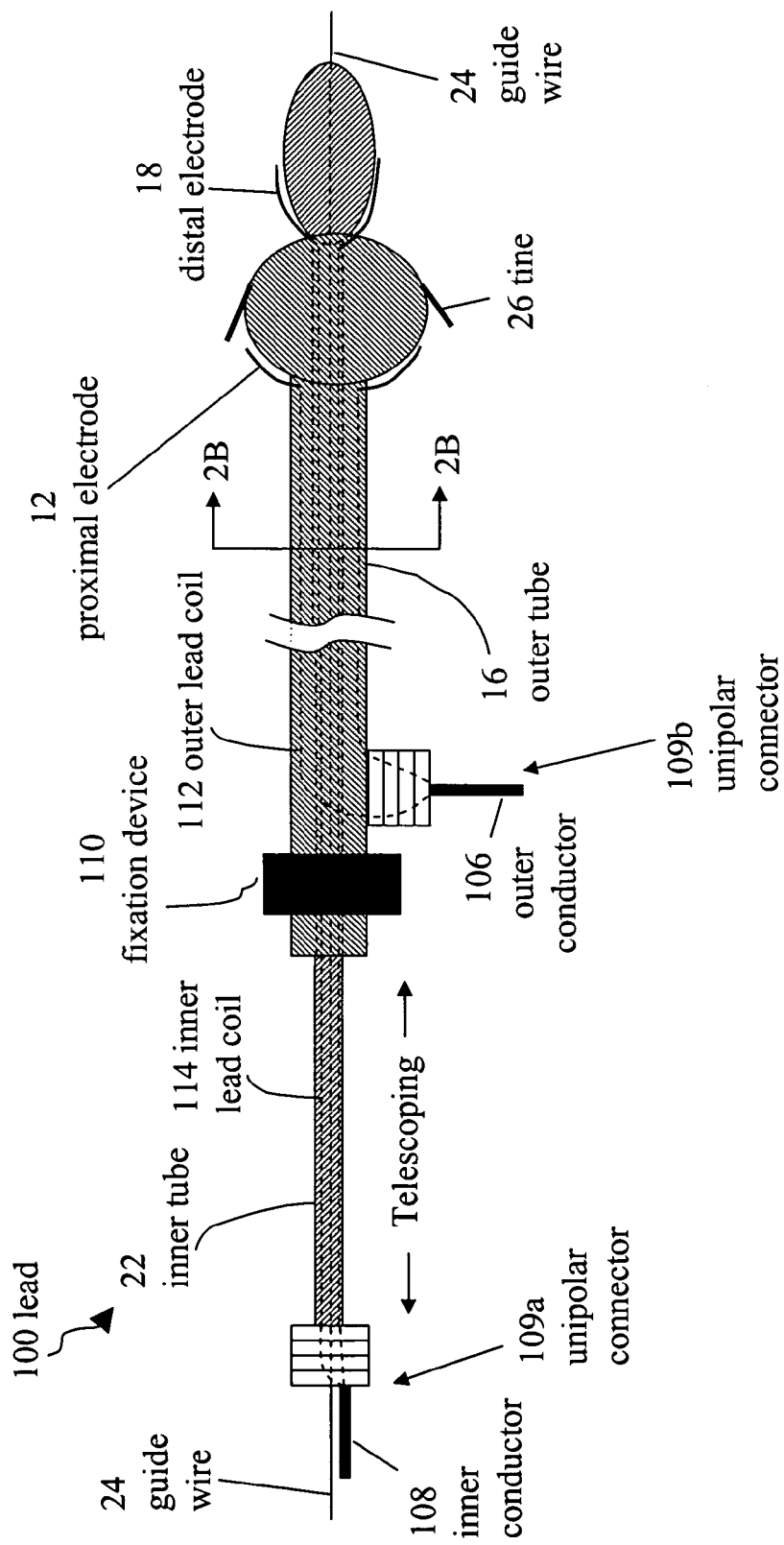
FIG. 2 is a cross-sectional side view of an example of the lead of FIG. 1A.

FIG. 1A shows a lead 10 that enables pacing of the heart from two separate sites. For example, the two separate sites can be the base and the apex of the LV of the heart. The lead 10 includes a proximal electrode 12 that is connected to an outer lead 14. In this example, the proximal electrode 12 enables pacing of the LV at a proximal portion of the coronary venous system such as the base of the LV. The outer lead 14 can be electrically connected to an electronic pacing control system (not shown). For example, the proximal electrode 12 can have a unipolar electrical connection with the control system. The outer lead 14 is embedded in an outer tube 16. The outer tube 16 provides a protective insulation layer around the outer lead 14. The proximal electrode 12 can be a conductive shell at the distal end of the outer tube 16. The oval-shaped appendage can include a radio-opaque or other marker for tracking the position of the proximal electrode 12. This marker can be detected using an x-ray emitter and detection system or other systems such as a fluoroscope. The proximal electrode 12 can be pushed to a location (e.g., in the base of the LV) and held in place by one or more tines 26 on the oval-shaped appendage.

The lead 10 also includes a distal electrode 18 that is connected to an inner lead 20. The inner lead 20 is embedded in an inner tube 22. The inner lead 20 can be electrically connected to an electronic pacing control system (not shown). For example, the distal electrode 18 can have a unipolar electrical connection with the control system. The inner tube 22 provides a protective insulation layer around the inner lead 20. The distal electrode 18 can be a conductive shell or individual wires around an oval-shaped appendage at the distal end of the inner tube 22. The oval-shaped appendage can include a contrast agent for tracking the position of the distal electrode 18. The contrast agent can be, e.g., a radio-opaque fluid or solid that can be detected using an x-ray emitter and detection system. The inner tube 22 is configured to slide inside the outer tube 16. The inner tube 22 is concentric with the outer tube 16. In one example (illustrated in FIG. 1A), the distal electrode 18 fits into a pocket 28 in the oval shaped appendage of the proximal electrode 12.

The lead 10 can be used to provide dual site LV pacing leads for biventricular pacemakers for congestive heart failure patients, and thus can be packaged together with such implantable pacemakers.

Referring also to FIG. 1B, the distal electrode 18 is designed to be telescoped distally beyond the proximal electrode 12. For example, after placing the proximal electrode 12 in a secure location (held in place by the tines 26 and/or the oval-shaped appendage), the distal electrode 18 can be manipulated into a distal branch of the cardiac venous tree such as the apex of the LV beyond the proximal electrode 12. The distal electrode 18 can be telescoped to an adjustable distance up to about five centimeters (cm) or more away from the proximal electrode 12.

The inner lead 20 can accommodate a guide wire 24 to enable positioning of the lead in a surgical area (e.g., the cardiac venous tree). In an example, the guide wire 24 is inserted first into a patient to a desired location and then the lead 10 is threaded along the guide wire 24 to the desired location. Subsequently, the guide wire 24 can be extended farther. The inner tube 22 with the embedded inner lead 20 is floppy and can be easily manipulated into the distal venous tree beyond the proximal electrode 12 by pushing the inner tube 22 along the guide wire 24.

The lead 10, with the inner tube 22 and the outer tube 16 being concentric, enables dual site pacing ability with a single surgical placement to the pacing sites of interest. The concentric design also enables the lead 10 to be inserted down narrow passageways of the cardiac venous tree with less twisting problems than, for instance, a lead with two leads side by side, because the concentric inner and outer tubes of the lead 10 bend together.

In use, the proximal and distal electrodes 12, 18 of the lead 10 can be electronically controlled to provide simultaneous or sequential pacing at two sites. In some examples, after placement, one of the proximal or distal electrodes (e.g., 12) can continue to pace a site of the heart even if there is a micro-dislodgement of the other electrode (e.g., 18) such that the other electrode cannot be used.

In other examples, the proximal and distal electrodes 12, 18 can also provide bipolar pacing to two sites by having one electrode serve as the anode and the other as the cathode. Referring to FIG. 2, a lead 100 is an example of the lead 10. The lead 100 includes an outer tube 16 with an embedded outer lead coil 112. The outer lead coil 112 is electrically connected to an outer conductor 106 of a first unipolar connector 109b. The lead 100 includes an inner tube 22 with an embedded inner lead coil 114. The inner lead coil 114 is electrically connected to an inner conductor 108 of a second unipolar connector 109a. The unipolar connectors 109a and 109b are configured to be connected to a pacing control system (not shown). In some exemplary embodiments, the unipolar connectors 109a and 109b comply with a pacing control system standard (e.g., the IS-1 international pace maker standard for bipolar connectors). Other examples of pacing control system standards for unipolar connectors include, but are not limited to VS-1, VS-1A, and VS-1B.

A fixation device 110 enables the surgeon to prevent motion of the distal electrode 18 relative to the proximal electrode 12 by locking the inner tube 22 against the outer tube 16. The fixation device 110 can be an external clamp around the outer tube 16.

Figure 3:
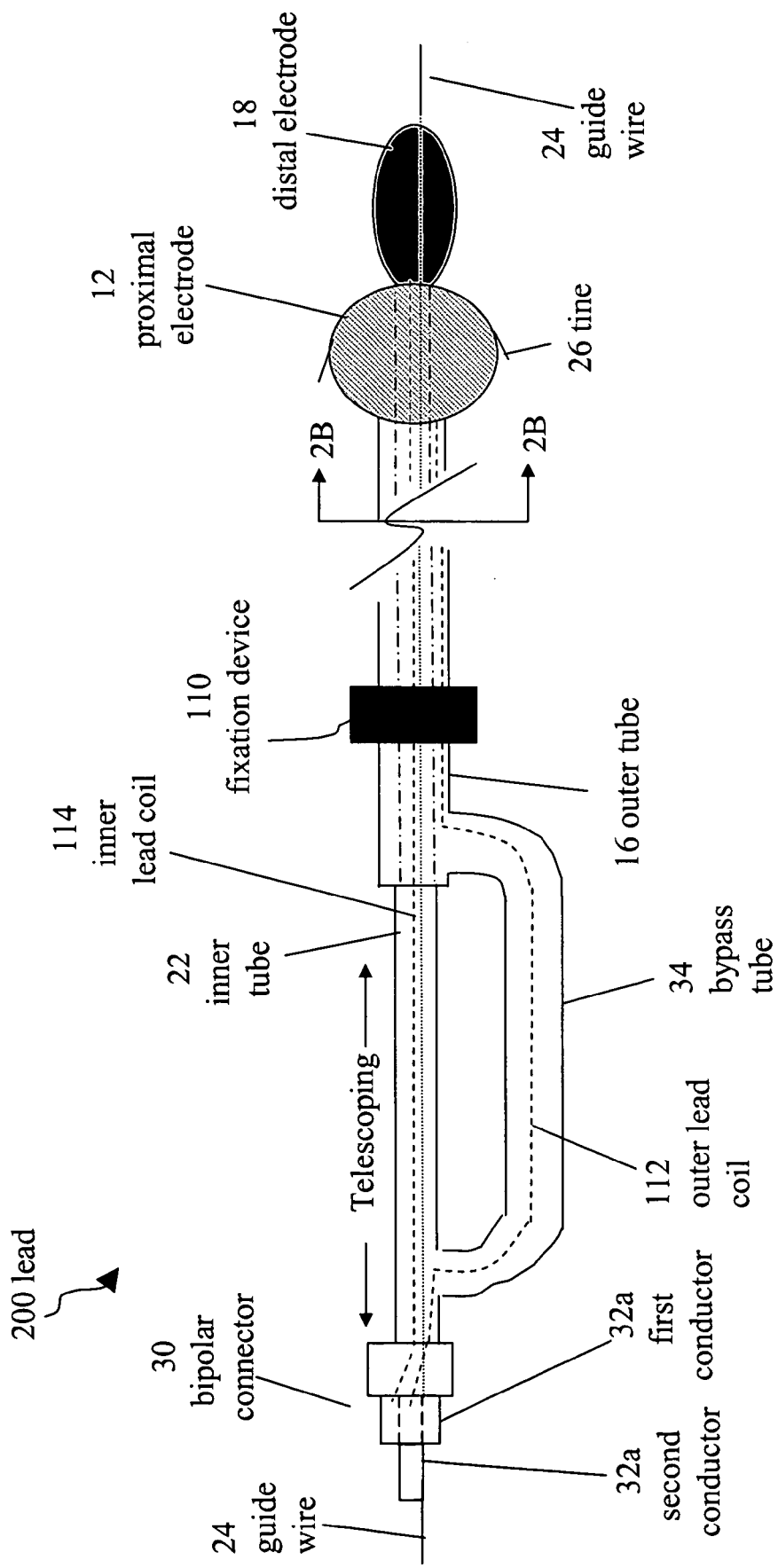
FIG. 3 is a cross-sectional side view of another example of the lead of FIG. 1A.

Referring to FIG. 3, an alternative embodiment of a lead 200 includes an inner tube 22, an outer tube 16, and a flexible bypass tube 34. A proximal end of the bypass tube 34 connects to the inner tube 22 at an opening in the wall of the inner tube 22. Similarly, a distal end of the bypass tube 34 connects to the outer tube 16 at an opening in the wall of the outer tube 16. The outer lead coil 112 passes through a portion of a lumen of the inner tube 22 before crossing over into a lumen of the bypass tube 34 through the opening in the wall of the inner tube 22. The outer lead coil 112 proceeds through the lumen of the bypass tube 34 before entering a lumen of the outer tube 16 through the opening in the wall of the outer tube 16. The outer lead coil 112 thus passes through the inner tube 22, the bypass tube 34, and the outer tube 16 before connecting to the proximal electrode 12. Meanwhile, the inner lead coil 114 passes through only the inner tube 22 before being connected to the distal electrode 18. The inner and outer lead coils 112 and 114 are attached to a bipolar connector 30 that is configured to connect to a pacing control system (not shown). The bipolar connector 30 carries separate signals from the pacing control system to the inner and outer lead coils 112 and 114. The bipolar connector 30 includes a first conductor 32a contacting the inner lead coil 114 and a second conductor 32b contacting the outer lead coil 112. The first and second conductors 32a and 32b are configured to be received by a port of the pacing control system from which electrical signals are transmitted. The first and second conductors 32a and 32b are electrically isolated from each other to reduce or prevent interference of the signals being transmitted from the port to the inner and outer lead coils 114 and 112. In some exemplary embodiments, the bipolar connector 30 complies with a pacing control system standard (e.g., the IS-1 international pace maker standard for bipolar connectors). Other examples of pacing control system standards for bipolar connectors include, but are not limited to VS-1, VS-1A, and VS-1B. In some embodiments, the first and second conductors 32a and 32b are arranged coaxially such that the first conductor 32a is surrounded by the second conductor 32b or vice versa. In some of these embodiments, a grounding sheath may surround the first and second conductors 32a and 32b. In additional embodiments, the first and second conductors 32a and 32b are arranged side-by-side in the center of bipolar connector 30. In this configuration, sometimes referred to as twinaxial, a grounding sheath surrounds an insulator, which in turn surrounds the first and second conductors 32a and 32b.

As with lead 100 (FIG. 2), the fixation device 110 of lead 200 enables a surgeon to prevent motion of the distal electrode 18 relative to the proximal electrode 12 by locking the inner tube 22 against the outer tube 16. The fixation device 110 can be an external clamp around the outer tube 16.

Figure 4:
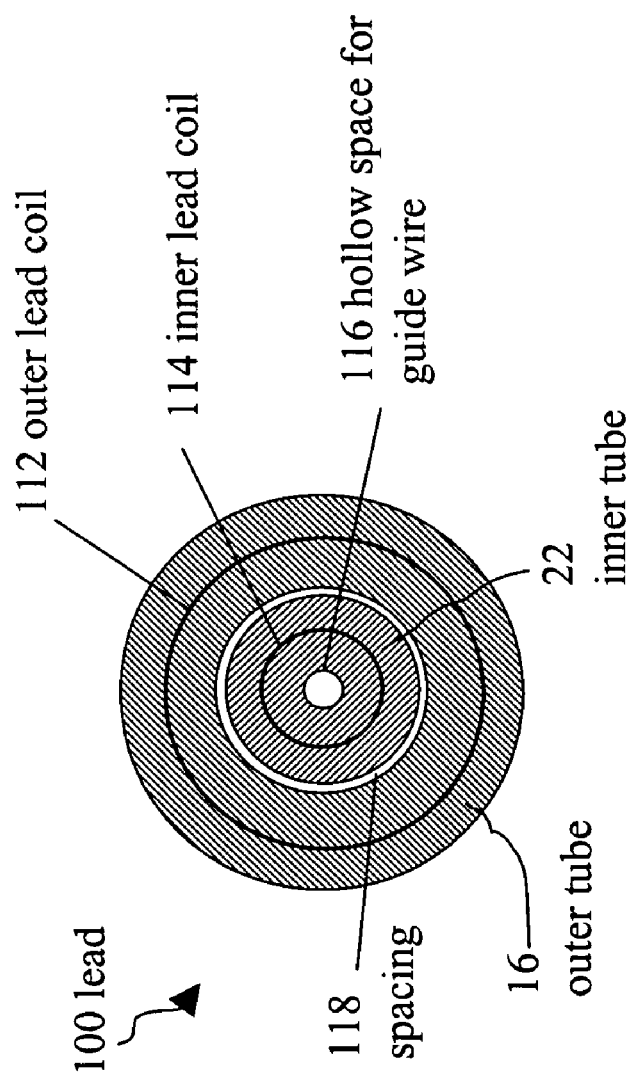
FIG. 4 is a transverse cross-sectional view of the lead of FIGS. 2 and 3.

Referring to FIG. 4, leads 100 and 200 include a hollow space 116 to receive the guide wire 24. The diameter of the hollow space 116 is adequate to receive the guide wire 24, which typically has a diameter between approximately 0.14 and 0.16 mm. The leads 100 and 200 also include a cylindrical spacing 118 between the inner tube 22 and the outer tube 16.

In some exemplary embodiments, the leads 100 and 200 are approximately 7 French (F) or 2.33 millimeter (mm) in diameter and range from approximately 6 F (2 mm) to 9 F (3 mm) in diameter. In other exemplary embodiments, the dimensions of leads 100 and 200 are adjusted according to a particular application. In one example, the lead 100 is approximately eighty centimeters (cm) in length, although shorter and longer lead lengths may also be used.

Suitable materials for the conductors 32a, 32b, 106, 108, 114, and 112 are standard electrically conducting materials that are lightweight and can be formed into wires and coils. For example, nickel alloys, such as Elgiloy® (an alloy of Ni, Co, Cr, Mo, Fe, Mn, C, and Be manufactured by Elgiloy Specialty Metals), and MP35N® (a nonmagnetic, nickel-cobalt-chromium-molybdenum alloy manufactured by SPS Technologies) can be used. Of note, these materials are often manufactured in a drawn-brazed-strand (DBS) technique with heated silver.

The electrodes 12 and 18 can be platinum alloy (e.g., platinum-iridium alloys) or any other conducting, medical grade materials that can be formed into a layer and are known to those skilled in the art. The materials for the electrodes must be compatible with biological contact because the electrodes are in long-term contact with tissue. For example, the electrodes can also be made of Elgiloy®, iridium oxide, platinum coated with platinized titanium, or of a titanium or graphite core coated with a vitreous or pyrolytic carbon coating. Of note, the above materials can also be coated with a steroid such as dexamethasone sodium phosphate.

Suitable materials for the inner, outer, and bypass tubes 22, 16, and 34 are medical grade polymers, e.g., alloys of silicone and polyurethane, which can be engineered to create a desired degree of flexibility for bending during surgery. The materials must also provide electric insulation. The materials must also have a low coefficient of friction between the inner and outer tubes to enable the inner tube 22 to easily slide against the outer tube 16.

Materials for the inner, outer, and bypass tubes 22, 16, and 34 include inherently lubricious plastic such as fluoropolymers. Examples of suitable fluoropolymers include polytetrafluoroethylene (PTFE), polyperfluoroalkoxy (PFA), fluorinated ethylene-propylene (FEP), and polyethylenechlorotrifluoroethylene (ECTFE). These fluoropolymers are available, for example, from Dupont® of Wilmington, Del. Another example of a suitable fluoropolymer is polyvinylidenefluoride (PVDF), available from Solvay® S.A. of Brussels in Belgium.

Another suitably inherently lubricious plastic is polyacetal. Examples of polyacetals include polyoxymethylene and ultrahigh molecular weight polyethylene (UHMWPE). Polyoxymethylene and UHMWPE are also available from Dupont® of Wilmington, Del.

The materials for the inner, outer, and bypass tubes 22, 16, and 34 also include insulated plastics of suitable flexibility that contain an additive to make them lubricious. For example, additives UHMWPE, polytetrafluoroethylene (PTFE), and silicone particles can make a plastic material more lubricious. The silicone additive is available from Dow Corning® of Midland, Mich.

The materials for the inner, outer, and bypass tubes 22, 16, and 34 also include plastics with modified surfaces. For example, a treatment available from Spire Corporation®, SPI-Polymer™, enhances the surface properties of medical grade polymers without affecting bulk properties using ion beam technology. The SPI-Polymer™ treatment generates a slippery surface on the medical grade polymers resulting in reduced tackiness and slick, low friction.

For another example, medical grade polymers can be silanized to make a hydrophobic surface that is lubricious. Silanization can involve activating a surface, for example, with sodium hydroxide (NaOH) to get oxygen ions (i.e., O—) on the surface and then reacting the surface with a silane, e.g., a chlorosilane, which becomes grafted to the surface.

Methods of Use of the Dual-Site Pacing Lead

Figure 5:
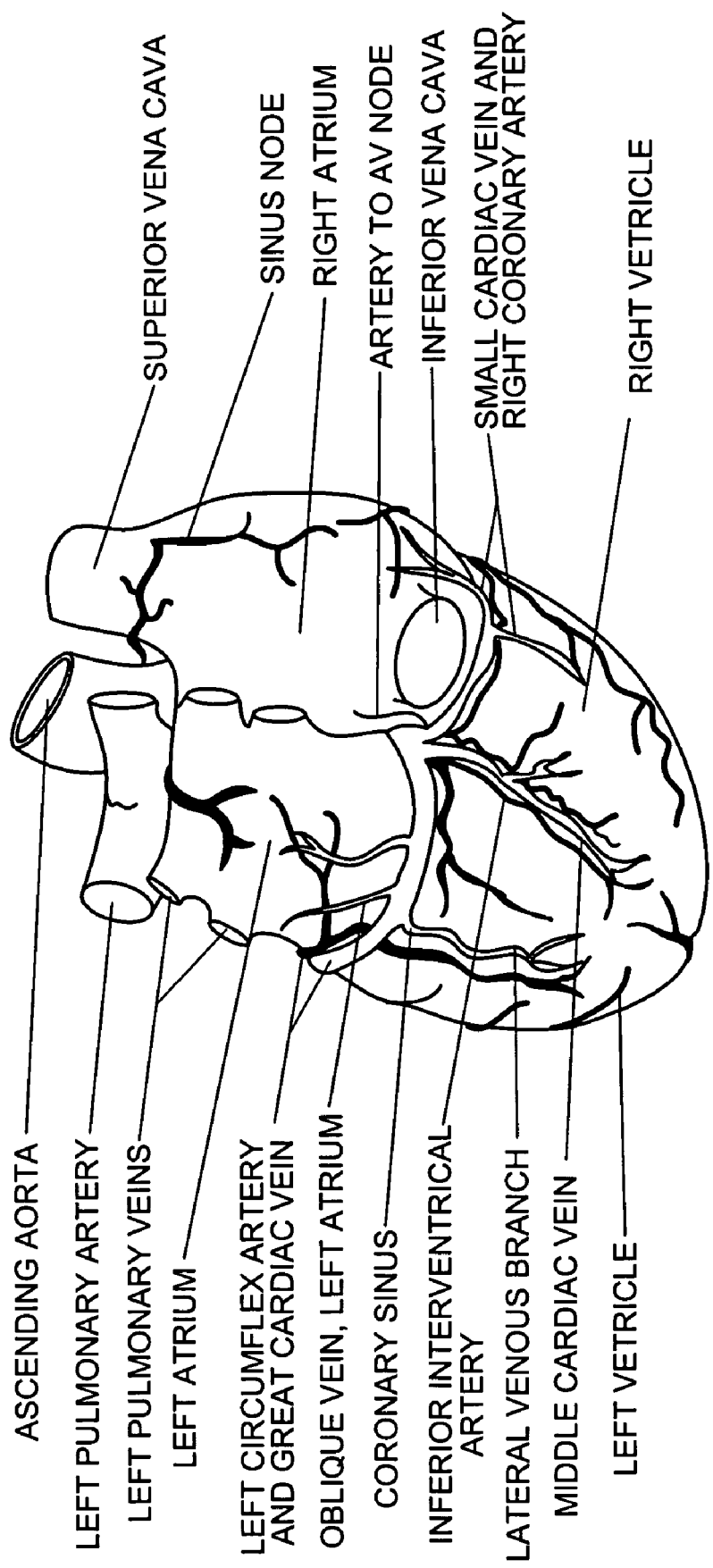
FIG. 5 is a diagram of a heart that shows the cardiac venous system and a left ventricle (LV).
Figure 6:
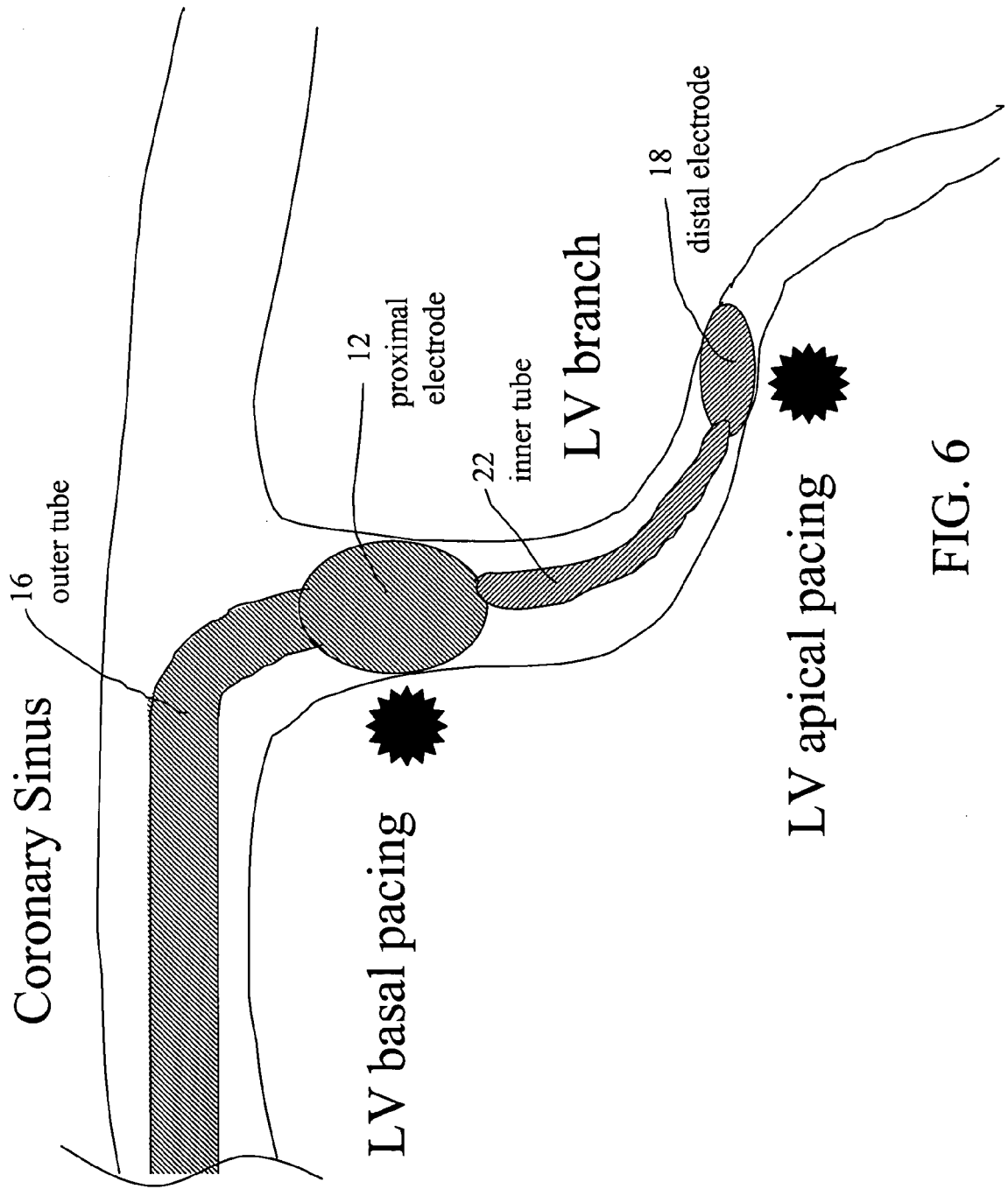
FIG. 6 is a cross-sectional view of the lead of FIG. 1A in a coronary sinus vein.

Referring to FIGS. 5 and 6, two branches of the coronary sinus in an area of interest for placement of one of the leads 10, 100, and 200 for a biventricular pacemaker are the various lateral venous branches. The guide wire 24, after being placed in the particular branch, can be used to insert one of the leads 10, 100, and 200 to a desired location in the particular branch.

One of the leads 10, 100, and 200 can be placed using the following technique. A small incision is made in an incision area in the chest wall just below the collarbone. A pocket is formed under the skin. A surgeon prepares the lead for insertion by positioning the distal electrode 18 next to the proximal electrode 12. A guiding sheath is first placed into the coronary sinus via the cephalic or subclavian vein, superior vena cava, and right atrium by standard techniques known to those in the field, and a coronary sinus venogram is typically obtained by injection of a radio-contrast agent and fluoroscopy to define the coronary venous anatomy and choose a suitable coronary sinus branch for lead placement. The guiding sheath is then used to place the lead into the coronary sinus. The guide wire 24 is then manipulated into the desired coronary venous branch with fluoroscopic guidance. The lead is then threaded over the guide wire 24 using the hollow space 116 by pushing the outer tube 16 until the proximal electrode 12 reaches the tributary branch of interest. During this pushing, the distal electrode 18 is pushed ahead of the proximal electrode 12 and the position of the proximal electrode 12 of the lead is tracked using the radio-opaque marker in the oval-shaped appendage of the proximal electrode 12 and contrasted with a previously measured intersection of the particular tributary branch. The proximal electrode 12 is pushed until a stable position in the tributary branch is reached with acceptable pacing parameters. The proximal electrode 12 is now in position for LV basal pacing.

For LV apical pacing in a particular tributary branch, the surgeon pushes guide wire 24 beyond the proximal electrode 12 into the tributary branch. Subsequently, the surgeon pushes the inner tube 22 on the guide wire 24 and slides the inner tube 22 inside the outer tube 16 such that the distal electrode 18 moves distally away from the proximal electrode 12. During this movement, the position of the distal electrode 18 is tracked using the aforementioned contrast agent in the oval shaped appendage of the distal electrode 18. When the distal electrode 18 is in a stable place at a desired apical pacing location with acceptable pacing parameters, the surgeon can lock the fixation device 110 to fix the position of the distal electrode 18 with respect to the proximal electrode 12. The oval-shaped appendage at the end of the inner tube 22 helps the distal electrode 18 to stay in place in the tributary branch. Subsequently, the guide wire 24 can be pulled out leaving the pacing electrodes 12, 18 in place. Given the correct placement of the pacing electrodes 12 and 18, the electrodes 12 and 18 can be used to treat heart conditions by simultaneous or sequential pacing to optimize LV apical and basal pacing delay for treatment of heart problems.

Alternate Applications

The new pacing leads can also be used, in addition to LV pacing, to treat neurologic, muscular, and gastrointestinal disorders. Specifically, the new leads can be used for tissue stimulation for neurologic disorders such as Parkinson's disease and paralysis, neuromuscular disorders such as multiple sclerosis and amyotrophic lateral sclerosis, and gastrointestinal disorders such as amotility.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An apparatus comprising:
a first tube;
a first lead conductor having a portion extending through the first tube;
a proximal electrode disposed at a distal end of the first tube, the proximal electrode being in electrical communication with the first lead conductor;
a second tube arranged slideably within the first tube, the second tube forming a central lumen sized to accommodate a guide wire;
a second lead conductor extending through the second tube;
a distal electrode disposed at a distal end of the second tube, the distal electrode being in electrical communication with the second lead conductor, wherein the proximal electrode has walls defining a cavity sized to receive at least a portion of the distal electrode and to prevent the distal electrode from moving into the first tube;
a bipolar connector attached to the first and second lead conductors and configured to be removably attached to a pacing control system; and
a third tube having proximal and distal ends, wherein the distal end of the third tube is attached to a portion of the first tube, the portion defining an opening in the first tube; the proximal end of the third tube is attached to a portion of the second tube, the portion defining an opening in the second tube; and the first lead conductor extends through portions of the first, second, and third tubes, and passes through the openings in the first and second tubes.

2. The apparatus of claim 1, wherein the connector is further configured to transmit first and second signals from the pacing control system to the first and second lead conductors, respectively.

3. The apparatus of claim 2, wherein the connector comprises:
first and second connecting conductors attached to the first and second lead conductors and configured to be received by a port in the pacing control system; and a housing at least partially enclosing the first and second connecting conductors.

4. The apparatus of claim 3, wherein the first and second connecting conductors are arranged coaxially.

5. The apparatus of claim 3, wherein the first and second connecting conductors are arranged twinaxially.

6. The apparatus of claim 2, wherein the connector complies with at least one of: an IS-1 international pace maker standard, a VS-1 standard, a VS-1A standard, and a VS-1B standard.

7. The apparatus of claim 1, wherein the second tube is longer than the first tube.

8. The apparatus of claim 1, wherein the distal end of the first tube comprises a first appendage, and wherein the proximal electrode is attached to an outer surface of the first appendage.

9. The apparatus of claim 8, wherein the distal end of the second tube comprises a second appendage, and wherein the distal electrode is attached to an outer surface of the second appendage.

10. The apparatus of claim 9, wherein the first and second appendages each comprises a radio-opaque marker.

11. The apparatus of claim 9, wherein at least one of the first and second appendages comprises a number of tines, the number being selected from a group consisting of one, and more than one.

12. The apparatus of claim 1, wherein the first lead conductor comprises a coil.

13. The apparatus of claim 1, wherein the second lead conductor comprises a coil.

14. The apparatus of claim 1, further comprising a fixation device to prevent motion of the second tube relative to the first tube.

15. The apparatus of claim 1, wherein the first and second lead conductors are bipolar.

16. The apparatus of claim 1, wherein the distal electrode can be extended approximately at least five centimeters beyond the proximal electrode.

17. The apparatus of claim 1, wherein the first and second tubes are electrically insulating.

18. An implantable biventricular pacemaker comprising the apparatus of claim 1.

19. An apparatus comprising:
a first tube;
a first lead conductor having a portion extending through the first tube;
a proximal electrode disposed at a distal end of the first tube, the proximal electrode being in electrical communication with the first lead conductor;
a second tube arranged slideably within the first tube, the second tube forming a central lumen sized to accommodate a guide wire;
a second lead conductor extending through the second tube;
an oval-shaped distal electrode disposed at a distal end of the second tube, the distal electrode being in electrical communication with the second lead conductor;
a bipolar connector attached to the first and second lead conductors and configured to be removably attached to a pacing control system; and
a third tube having proximal and distal ends wherein:
the distal end of the third tube is attached to a portion of the first tube, the portion defining an opening in the first tube;
the proximal end of the third tube is attached to a portion of the second tube, the portion defining an opening in the second tube; and
the first lead conductor extends through portions of the first, second, and third tubes, and passes through the openings in the first and second tubes.

20. An apparatus comprising:
a first tube;
a first lead conductor having a portion extending through the first tube;
a proximal electrode disposed at a distal end of the first tube, the proximal electrode being in electrical communication with the first lead conductor;
a second tube arranged slideably within the first tube, the second tube forming a central lumen sized to accommodate a guide wire;
a second lead conductor extending through the second tube;
a distal electrode disposed at a distal end of the second tube, the distal electrode being in electrical communication with the second lead conductor;
a bipolar connector attached to the first and second lead conductors and configured to be removably attached to a pacing control system; and
a third tube having proximal and distal ends wherein:
the distal end of the third tube is attached to a portion of the first tube, the portion defining an opening in the first tube;
the proximal end of the third tube is attached to a portion of the second tube, the portion defining an opening in the second tube; and
the first lead conductor extends through portions of the first, second, and third tubes, and passes through the openings in the first and second tubes.

* * * * *